(12) United States Patent
Man et al.

(10) Patent No.: US 6,326,388 B1
(45) Date of Patent: Dec. 4, 2001

(54) SUBSTITUTED 1,3,4-OXADIAZOLES AND A METHOD OF REDUCING TNF-ALPHA LEVEL

(75) Inventors: Hon-Wah Man, Neshanic Station; George W. Muller, Bridgewater, both of NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

(21) Appl. No.: 09/470,203

(22) Filed: Dec. 21, 1999

(51) Int. Cl.$^7$ ...................... A61K 31/4245; A61K 31/47; C07D 271/10
(52) U.S. Cl. ........................... 514/364; 548/131; 546/134
(58) Field of Search ........................... 548/131; 514/364, 514/307; 546/134

(56) References Cited

U.S. PATENT DOCUMENTS

| | | |
|---|---|---|
| 4,173,652 | 11/1979 | Bruins et al. . |
| 4,556,673 | 12/1985 | Anderson et al. . |
| 4,820,828 | 4/1989 | Demers et al. . |
| 5,525,619 * | 6/1996 | Koeing et al. ........................ 514/364 |
| 5,605,914 | 2/1997 | Muller . |
| 5,658,940 | 8/1997 | Muller et al. . |
| 5,670,526 * | 9/1997 | Dodd et al. ........................... 514/340 |
| 5,698,579 | 12/1997 | Muller . |
| 5,703,098 | 12/1997 | Muller et al. . |
| 5,728,844 | 3/1998 | Muller et al. . |
| 5,728,845 | 3/1998 | Muller et al. . |
| 5,736,570 | 4/1998 | Muller et al. . |
| 5,801,195 | 9/1998 | Muller et al. . |
| 5,877,200 | 3/1999 | Muller et al. . |
| 5,929,117 | 7/1999 | Muller et al. . |
| 5,968,945 | 10/1999 | Muller et al. . |
| 6,011,050 | 1/2000 | Muller et al. . |
| 6,020,358 | 2/2000 | Muller et al. . |
| 6,034,113 * | 3/2000 | Hewawasam et al. ............... 514/364 |
| 6,046,221 | 4/2000 | Muller et al. . |
| 6,075,041 | 6/2000 | Muller . |
| 6,153,628 * | 11/2000 | Jin et al. ............................... 514/340 |

FOREIGN PATENT DOCUMENTS

| | | |
|---|---|---|
| PCT/US97/00264 | 1/1997 | (EP) . |
| WO 97/05105 | 2/1997 | (EP) . |

OTHER PUBLICATIONS

A. De, U. et al., (2/75), "Possible Antineoplastic Agents I", *Journal of Pharmaceutical Sciences*, vol. 64(2), pp. 262–266.

Barnes, P.J., (1995) "Cyclic nucleotides and phosphodiesterases and airway function",*Eur Respir. J.* vol. 8, pp. 457–462.

Bazzoni, Flavia, et al., (Jun. 26, 1996), "The Tumor Necrosis Factor Ligand And Receptor Families", *Seminars in Medicine of the Beth Israel Hospital, Boston*, Flier, Jeffrey S., et al, Ed., vol. 331, No. 26, pp. 1717–1725.

Burnouf, Catherine, et al., (1998), "Chapter 10: Phosphodiesterases 4 Inhibitors", *Annual Reports in Medicinal Chemistry*, Doherty, Ed., vol. 33, pp. 91–109.

Buu–Ho, Nouyen P. et al., (3/70), "Synthesis and Pharmacological Properties of Substituted Cinnamohydroxamic Acids", *JMC*, vol. 13(2), pp. 211–213.

Badger, Alison M. et al., (10/97), "Advances in antiarthritic therapeutics", *DDT*, vol. 2, No. 10, pp. 427–435.

Beutler, Bruce et al., (1993), "Tumor Necrosis Factor in the pathogenesis of infectious diseases", *Critical Care Medicine*, vol. 21, No. 10, pp. S423–S435.

Corral, Laura G., et al., (7/96), "Selection of Novel Analogs of Thalidomide with Enhanced Tumor Necrosis Factor αInhibitory Activity", *Molecular Medicine*, vol. 2, No. 4, pp. 1076–1551.

deBrito, FB et al., (1997) "Type 4 Phosphodiesterase Inhibitors and their Potential in the Treatment of Inflammatory Disease", *Emerging Drugs*, vol. 2, pp. 249–268.

Denis, L.J., et al., (1997) "Matrix Metalloproteinase Inhibitors: Present Achievements and Future Prospects", *Investigational New Drugs*, vol. 15, pp. 175–185.

Eger, K. et al., (1990), "Synthesis, Central Nervous System Activity and Teratogenicity of a Homothalidomide", *Arzneim–Forsch/Drug Res*, vol. 40(II), Nr. 10 pp. 1073–1075.0.

Friderichs, Von E., (1982), "Untersuchungen zum ZNS–Wirkprofil von Thalidomid–Analoga", *Arzhelm–Forsch./Drug Res.*, vol. 32(1), No. 6, pp. 613–620.

Hart, David J. et al., (1983) "Preparation of Primary Amines and 2–Azetidinones via N–Trimethylsilyl Imines", *J. Org. Chem.*, vol. 48, pp. 289–294.

Hughes, Bernadette, et al., (3/97) "PDE 4 inhibitors: the use of molecular cloning in the design and development of novel drugs", *DDT*, vol. 2, No. 3, pp. 89–101.

Kleinman, Edward F., et al., (1998), "Striking Effect of Hydroxamic Acid Substitution on the Phosphodiesterase Type 4 (PDE4) and TNF α Inhibitory Activity of Two Series of Rolipram Analogues: Implications for a New Active Site Model of PDE4.", *J. Med. Chem.*, vol. 41, pp. 266–270.

Lombardo, Louis J., (9/95), "Anti–Inflammatory & Anti–Allergy Agents", *Current Pharmaceutical Design*, Weichman, Barry M., Ed., vol. 1, No. 2, pp. 255–268.

Lee, John C. et al., (1995), "Low–Molecular–Weight TNF Biosynthesis Inhibitors: Strategies and Prospectives", *Circulatory Shock*, vol. 44, pp. 97–103.

Levy, Daniel E., et al., (1998), "Matrix metalloproteinase inhibitors: A Structure–Activity Study", *J. Med Chem.*, vol. 41, pp. 199–223.

(List continued on next page.)

*Primary Examiner*—Floyd D. Higel
*Assistant Examiner*—Kamal Saeed
(74) *Attorney, Agent, or Firm*—Mathews, Collins, Shepherd & Gould, P.A.

(57) ABSTRACT

Substituted 1,3,4-oxadiazole compounds reduce the levels of TNFα in a mammal. Typical embodiments are 2-[1-(3-cyclopentyloxy-4-methoxyphenyl)-2-(1,3,4-oxadiazol-2-yl) ethyl]-5-methylisoindoline-1,3-dione and 2-[1-(3-ethoxy-4-methoxyphenyl)-2-(1,3,4-oxadiazol-2-yl)ethyl]isoindoline-1,3-dione.

26 Claims, No Drawings

OTHER PUBLICATIONS

Müller, Thomas et al., (8/96) "Subtypes of the type 4 cAMP phosphodiesterases: structure, regulation and selective inhibition", *TIPS*, vol. 17, pp. 294–298.

Marriott, J. Blake, (1997), "TNF–α antagonists: monoclonal antibodies, soluble receptors, thalidomide and other novel approaches", *Exp. Opin. Invest. Drugs*, vol. 6(8), pp. 1105–1108.

Muller, George W., et al, (1998), "Thalidomide Analogs and PDE4 Inhibition", *Bioorganic & Medicinal Chemistry Letters*, vol. 8, pp. 2669–2674.

Muller, George W., et al. (1996), "Structural Modifications of Thalidomide Produce Analogs with Enhanced Tumor Necrosis Factor Inhibitory Activity", *Journal of Medicinal Chemistry*, vol. 39, No. 17, pp. 3238–3240.

Natchus, Michael G., et al., (1998), "Design and Synthesis of Conformationally–Constrained MMP Inhibitors", *Bioorganic & Medicinal Chemistry Letters*, vol. 8, pp. 2077–2080.

Naafs, B., et al., (3/85), "Thalidomide Therapy, An Open Trial", *International Journal of Dermatology*, vol. 24(2), pp. 131–134.

Palfreyman, Malcolm N., (1995) "Phosphodiesterase type IV inhibitors as Anti–Inflammatory agents", *Drugs of the Future*, vol. 30(8), pp. 793–804.

Palacios, Jose Maria, et al., (1995), "Second Messenger Systems as Targets for new Therapeutic Agents: Focus on Selective Phosphodiesterase Inhibitors", *Il Farmaco*, vol. 50(12), pp. 819–827.

Summers, James B., et al, (1998), "Matrix Metalloproteinase Inhibitors and Cancer", *Annual Reports In Medicinal Chemistry*, vol. 33, pp. 131–140.

Steinman, Douglas H. et al, (1998), "The Design, Synthesis, and Structure–Activity Relationships of a Series of Macrocyclic MMP Inhibitors", *Bioorganic & Medicinal Chemistry Letters*, vol. 8, pp. 2087–2092.

Strieter, Robert M. et al., (1993), "Role of tumor necrosis factor–α in disease states and inflammation", *Critical Care Medicine*, vol. 21, No. 10, pp. S447–S463.

Torphy, Theodore J. et al., (5/93) "Novel Phosphodiesterase Inhibitors for the Therapy of Asthma", *DN&P* vol. 6(4), pp. 203–214.

Torphy, Theodore J. et al., (1998) "Phosphodiesterase Isozymes, Molecular Targerts for Novel Antiasthma Agents", *Am J. Resp. Crit. Care Med.*, vol. 157, pp. 351–370.

Torphy, Theodore J., (1997), "Phosphodiesterase inhibitors", *Asthma*, Barnes, P.J. et al., pp. 1755–1773.

Teixeira, Mauro M. et al., (5/97) "Phosphodiesterase (PDE)4 inhibitors:anti–inflammatory drugs of the future", *TIPS*, vol. 18, pp. 164–170.

Tracey, Kevin J. et al, (1993), "Tumor Necrosis Factor, Other Cytokines and Disease", *Annu. Rev. Cell Biol.* vol. 9, pp. 317–343.

Tanaka, Kuntyoshi, et al., (1983), "Syntheses and Anti–Inflammatory and Analgesic Activities of Hydroxamic Acids and Acid Hydrazides", *Chem. Pharm. Bull*, vol. 31(8), pp. 2810–2819.

Wojtowicz–Praga, Slawomir M., et al., (1997), "Matrix metalloproteinase inhibitors", *Investigational New Drugs*, vol. 15, pp. 61–75.

Yu, Anita E., et al., (9/97), "Matrix Metalloproteinases, Novel Targets for Directed Cancer Therapy", *Drugs & Aging*, vol. 11(3), pp. 229–244.

I.C. Crocker and R.G. Townley, "Therapeutic potential of Phosphodiesterase 4 inhibitors in allergic diseases," Drug of Today, 35(7):519–535 (1999).

P. Norman, "PDE4 inhibitors 1999," Exp. Opin. Ther. Patents vol. 9(8):1101–1118 (1999).

* cited by examiner

SUBSTITUTED 1,3,4-OXADIAZOLES AND A METHOD OF REDUCING TNF-ALPHA LEVEL

FIELD OF THE INVENTION

The present invention relates to substituted 1,3,4-oxadiazole compounds, the method of reducing levels of tumor necrosis factor α and increasing cAMP levels and treating inflammatory and autoimmune diseases and cancer in a mammal through the administration thereof, and to pharmaceutical compositions of such derivatives.

BACKGROUND OF THE INVENTION

Tumor necrosis factor-α (TNFα) is a cytokine which is released primarily by cells of immune systems in response to certain immunostimulators. When administered to animals or humans, it causes inflammation, fever, cardiovascular effects, hemorrhage, coagulation, cachexia, and acute phase responses similar to those seen during acute infections, inflammatory diseases, and shock states. Excessive or unregulated TNFα production has been implicated in a number of disease conditions. These include endotoxemia and/or toxic shock syndrome [Tracey, et al., Nature 330, 662–664 (1987) and Hinshaw, et al., Circ. Shock 30, 279–292 (1990)], rheumatoid arthritis, inflammatory bowel disease, cachexia [Dezube, et al., Lancet, 335 (8690), 662 (1990)], and lupus. TNFα concentration in excess of 12,000 pg/mL have been detected in pulmonary aspirates from Adult Respiratory Distress Syndrome (ARDS) patients [Millar, et al., Lancet 2(8665), 712–714 (1989)]. Systemic infusion of recombinant TNFα resulted in changes typically seen in ARDS [Ferrai-Baliviera, et al., Arch. Surg. 124(12), 1400–1405 (1989)].

TNFα appears to be involved in a number of bone resorption diseases, including arthritis. When activated, leukocytes will produce bone-resorption. TNFα apparently contributes to this mechanism. [Bertolini, et al., Nature 319, 516–518 (1986) and Johnson, et al., Endocrinology 124(3), 1424–1427 (1989)]. TNFα also has been shown to stimulate bone resorption and inhibit bone formation in vitro and in vivo through stimulation of osteoclast formation and activation combined with inhibition of osteoblast functions. Another compelling link with disease is the association between production of TNFα by tumor or host tissues and malignancy associated hypercalcemia [Calci. Tissue Int. (US) 46(Suppl.), S3–10 (1990)]. In Graft versus Host Reactions, increased serum TNFα levels have been associated with major complication following acute allogenic bone marrow transplants [Holler, et al., Blood, 75(4), 1011–1016 (1990)].

Validation of TNF-α inhibition as a clinical therapy has been demonstrated by the therapeutic use of TNF-α antibodies and soluble TNF-α receptors. TNFα blockage with monoclonal anti-TNFα antibodies has been shown to be beneficial in rheumatoid arthritis [Elliot, et al., Int. J. Pharmac. 1995 17(2), 141–145]. High levels of TNFα are associated with Crohn's disease [von Dullemen, et al., Gastroenterology, 1995 109(1), 129–135] treatment with soluble TNFα receptor treatment gave clinical benefits.

Cerebral malaria is a lethal hyperacute neurological syndrome associated with high blood levels of TNFα and the most severe complication occurring in malaria patients. Elevated levels of serum TNFα correlated directly with the severity of disease and the prognosis in patients with acute malaria attacks [Grau, et al., N. Engl. J. Med. 320(24), 1586–1591 (1989)].

TNFα plays a role in the area of chronic pulmonary inflammatory diseases. The deposition of silica particles leads to silicosis, a disease of progressive respiratory failure caused by a fibrotic reaction. Antibodies to TNFα completely blocked the silica induced lung fibrosis in mice [Pignet, et al., Nature, 344, 245–247 (1990)]. High levels of TNFα production (in the serum and in isolated macrophages) have been demonstrated in animal models of silica and asbestos induced fibrosis [Bissonnette, et al., Inflammation 13(3), 329–339 (1989)]. Alveolar macrophages from pulmonary sarcoidosis patients have also been found to spontaneously release massive quantities of TNFα as compared with macrophages from normal donors [Baughman, et al., J. Lab. Clin. Med. 115(1), 36–42 (1990)].

Elevated levels of TNFα are implicated in reperfusion injury, the inflammatory response which follows reperfusion, and is a major cause of tissue damage after blood flow loss [Vedder, et al., PNAS 87, 2643–2646 (1990)]. TNFα also alters the properties of endothelial cells and has various pro-coagulant activities, such as producing an increase in tissue factor pro-coagulant activity, suppressing the anticoagulant protein C pathway, and down-regulating the expression of thrombomodulin [Sherry, et al., J. Cell Biol. 107, 1269–1277 (1988)]. TNFα has pro-inflammatory activities which together with its early production (during the initial stage of an inflammatory event) make it a likely mediator of tissue injury in several important disorders including but not limited to, myocardial infarction, stroke and circulatory shock. TNFα-induced expression of adhesion molecules, such as intercellular adhesion molecules (ICAM) or endothelial leukocyte adhesion molecules (ELAM) on endothelial cells may be especially important [Munro, et al., Am. J. Path. 135(1), 121–132 (1989)].

It has been reported that TNFα is a potent activator of retrovirus replication including activation of HIV-1. [Duh, et al., Proc. Nat. Acad. Sci. 86, 5974–5978 (1989); Poll, et al., Proc. Nat. Acad. Sci. 87, 782–785 (1990); Monto, et al., Blood 79, 2670 (1990); Clouse, et al., J. Immunol. 142, 431–438 (1989); Poll, et al., AIDS Res. Hum. Retrovirus, 191–197 (1992)]. At least three types or strains of HIV (i.e., HIV-1, HIV-2 and HIV-3) have been identified. As a consequence of HIV infection, T-cell mediated immunity is impaired and infected individuals manifest severe opportunistic infections and/or unusual neoplasms. HIV entry into the T-lymphocyte requires T-lymphocyte activation. Other viruses, such as HIV-1, HIV-2 infect T-lymphocytes after T-cell activation. This virus protein expression and/or replication is mediated or maintained by this T-cell activation. Once an activated T-lymphocyte is infected with HIV, the T-lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T-lymphocyte activation. Therefore, interference with cytokine activity such as prevention or inhibition of cytokine production, notably TNFα, in an HIV-infected individual assists in limiting the maintenance of T-lymphocyte caused by HIV infection.

Monocytes, macrophages, and related cells, such as kupffer and glial cells, also have been implicated in maintenance of the HIV infection. These cells, like T-cells, are targets for viral replication and the level of viral replication is dependent upon the activation state of the cells. [Rosenberg, et al., The immunopathogenesis of HIV Infection, Advances in Immunology, 57 (1989)]. Cytokines, such as TNFα, have been shown to activate HIV replication in monocytes and/or macrophages [Poli, et al., *Proc. Natl. Acad. Sci.*, 87, 782–784 (1990)], therefore, prevention or inhibition of cytokine production or activity aids in limiting HIV progression for T-cells. Additional studies have identified TNFα as a common factor in the activation of HIV in vitro and have provided a clear mechanism of action via a nuclear regulatory protein found in the cytoplasm of cells [Osborn, et al., *PNAS* 86 2336–2340]. This evidence suggests that reducing TNFα synthesis may have an antiviral effect in HIV infections, by reducing transcription and thus virus production.

AIDS viral replication of latent HIV in T-cell and macrophage lines can be induced by TNFα [Folks, et al., *PNAS* 86, 2365–2368 (1989)]. A molecular mechanism for the virus inducing activity is suggested by TNFα's ability to activate a gene regulatory protein (transcription factor, NFκB) found in the cytoplasm of cells, which promotes HIV replication through binding to a viral regulatory gene sequence (LTR) [Osborn, et al., *PNAS* 86, 2336–2340 (1989)]. TNFα in AIDS associated cachexia is suggested by elevated serum TNFα and high levels of spontaneous TNFα production in peripheral blood monocytes from patients [Wright, et al., *J. Immunol.* 141(1), 99–104 (1988)]. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227–29). NFκB has been implicated as a transcriptional activator in a variety of disease and inflammatory states and is thought to regulate cytokine levels including but not limited to TNFα and active HIV transcription [Dbaibo, et al., *J. Biol. Chem.* 1993, 17762–66; Duh, et al., *Proc. Natl. Acad. Sci.* 1989, 86, 5974–78; Bachelerie, et al., *Nature* 1991, 350, 709–12; Boswas, et al., *J. Acquired Immune Deficiency Syndrome* 1993, 6, 778–786; Suzuki, et al., *Biochem. And Biophys. Res. Comm.* 1993, 193, 277–83; Suzuki, et al., *Biochem. And Biophys. Res Comm.* 1992, 189, 1709–15; Suzuki, et al., *Biochem. Mol. Bio. Int.* 1993, 31(4), 693–700; Shakhov, et al., *Proc. Natl. Acad. Sci. USA* 1990,171, 35–47; and Staal, et al., *Proc. Nati. Acad. Sci. USA* 1990, 87, 9943–47]. Thus, it would be helpful to inhibit NFκB activation, nuclear translation or binding to regulate transcription of cytokine gene(s) and through this modulation and other mechanisms be useful to inhibit a multitude of disease states.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators, including TNFα and NFκB. Increased levels of cAMP also lead to the relaxation of airway smooth muscle.

The primary cellular mechanism for the inactivation of cAMP is the breakdown of cAMP by a family of isoenzymes referred to as cyclic nucleotide phosphodiesterases (PDE) [Beavo and Reitsnyder, *Trends in Pharm.*, 11, 150–155, 1990]. There are ten known members of the family of PDEs. It is well documented that the inhibition of PDE type IV (PDE 4) enzyme is particularly effective in both the inhibition of inflammatory mediator release and the relaxation of airway smooth muscle [Verghese, et al., *Journal of Pharmacology and Experimental Therapeutics*, 272(3), 1313–1320, 1995].

Decreasing TNFα levels and/or increasing cAMP levels thus constitutes a valuable therapeutic strategy for the treatment of many inflammatory, infectious, immunological, and malignant diseases. These include but are not restricted to: septic shock, sepsis, endotoxic shock, hemodynamic shock and sepsis syndrome, post ischemic reperfusion injury, malaria, mycobacterial infection, meningitis, psoriasis and other dermal diseases, congestive heart failure, fibrotic disease, cachexia, graft rejection, cancer, tumor growth, undesirable angiogenesis, autoimmune disease, opportunistic infections in AIDS, rheumatoid arthritis, rheumatoid spondylitis, osteoarthritis, other arthritic conditions, inflammatory bowel disease, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies [Beutler, et al., *Science* 234, 470–474 (1985); WO 92/11383].

Angiogenesis, the process of new blood vessel development and formation, plays an important role in numerous normal and pathological physiological events. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary. Angiogenesis is required for tumor growth beyond a certain size.

Inhibitory influences predominate in the naturally occurring balance between endogenous stimulators and inhibitors of angiogenesis [Rastinejad, et al., 1989, *Cell* 56:345–355]. In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis [Moses, et al., 1991, *Biotech*. 9:630–634; Folkman, et al., 1995, *N. Engl. J. Med.*, 333:1757–1763; Auerbach, et al., 1985, *J. Microvasc. Res.* 29:401–411; Folkman, 1985, *Advances in Cancer Research*, eds. Klein and Weinhouse, Academic Press, New York, pp. 175–203; Patz, 1982, *Am. J. Opthalmol.* 94:715–743; and Folkman, et al., 1983, *Science* 221:719–725]. In a number of pathological conditions, the process of angiogenesis contributes to the disease state. For example, significant data suggests that the growth of solid tumors is dependent on angiogenesis [Folkman and Klagsbrun, 1987, *Science* 235:442–447].

The maintenance of the avascularity of the cornea, lens, and trabecular meshwork is crucial for vision as well as for ocular physiology. See, e.g., reviews by Waltman, et al., 1978, *Am. J. Ophthal.* 85:704–710 and Gartner, et al., 1978, *Surv. Ophthal.* 22:291–312. Currently, the treatment of these diseases, especially once neovascularization has occurred, is inadequate and blindness often results.

An inhibitor of angiogenesis could have an important therapeutic role in limiting the contributions of this process to pathological progression of the underlying disease states as well as providing a valuable means of studying their etiology. For example, agents that inhibit tumor neovascularization could play an important role in inhibiting metastatic and solid tumor growth.

Several kinds of compounds have been used to prevent angiogenesis. Taylor, et al. used protamine to inhibit angiogenesis, [Taylor, et al., *Nature* 297:307 (1982)]. The toxicity of protamine limits its practical use as a therapeutic. Folkman, et al. used heparin and steroids to control angiogenesis. [Folkman, et al., *Science* 221:719 (1983) and U.S. Pat. Nos. 5,001,116 and 4,994,443]. Steroids, such as tetrahydrocortisol, which lack gluco and mineral corticoid activity, are angiogenic inhibitors. Interferon β is also a potent inhibitor of angiogenesis induced by allogeneic spleen cells [Sidky, et al., *Cancer Research* 47:5155–5161 (1987)]. Human recombinant interferon-α was reported to be successfully used in the treatment of pulmonary hemangiomatosis, an angiogenesis-induced disease [White, et al., *New England J. Med.* 320:1197–1200 (1989)].

Other agents which have been used to inhibit angiogenesis include ascorbic acid ethers and related compounds [Japanese Kokai Tokkyo Koho No. 58-131978]. Sulfated polysaccharide DS 4152 also shows angiogenic inhibition [Japanese Kokai Tokkyo Koho No. 63-119500]. A fungal product, fumagillin, is a potent angiostatic agent in vitro. The compound is toxic in vivo, but a synthetic derivative, AGM 12470, has been used in vivo to treat collagen II arthritis. Fumagillin and o-substituted fumagillin derivatives are disclosed in EPO Publication Nos. 0325199A2 and 0357061A1.

In U.S. Pat. No. 5,874,081, Parish teaches use of monoclonal antibodies to inhibit angiogenesis. In WO92/12717, Brem, et al. teach that some tetracyclines, particularly Minocycline, Chlortetracycline, Demeclocycline and Lymecycline are useful as inhibitors of angiogenesis. Brem, et al. teach that Minocycline inhibits angiogenesis to an extent comparable to that of the combination therapy of heparin and cortisone [*Cancer Research*, 51, 672–675, Jan. 15, 1991]. Teicher, et al. teach that tumor growth is decreased and the number of metastases is reduced when the antiangiogenic agent of metastases is reduced when the antiangiogenic agent Minocycline is used in conjunction with cancer chemotherapy or radiation therapy [*Cancer Research*, 52, 6702–6704, Dec. 1, 1992].

Macrophage-induced angiogenesis is known to be stimulated by TNFα. Leibovich, et al. reported that TNFα induces in vivo capillary blood vessel formation in the rat cornea and the developing chick chorioallantoic membranes at very low doses and suggested TNFα is a candidate for inducing angiogenesis in inflammation, wound repair, and tumor growth [*Nature*, 329, 630–632 (1987)].

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, brain cancer, melanoma, lymphoma, erythroleukemia, uterine cancer, bone cancer, and head and neck cancer.

Cancer is now primarily treated with one or a combination of three types of therapies: surgery, radiation, and chemotherapy. Surgery involves the bulk removal of diseased tissue. While surgery is sometimes effective in removing tumors located at certain sites (e.g., in the breast, colon, and skin) surgery cannot be used in the treatment of tumors located in other areas (e.g., the backbone) nor in the treatment of disseminated neoplastic conditions (e.g., leukemia). Chemotherapy involves the disruption of cell replication or cell metabolism. Chemotherapy is used most often in the treatment of leukemia, as well as breast, lung, and testicular cancer.

Chemotherapeutic agents are often referred to as antineoplastic agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Antimetabolites are typically reversible or irreversible enzyme inhibitors, or compounds that otherwise interfere with the replication, translation or transcription of nucleic acids. Thus, it would be preferable to find less toxic compounds for cancer treatment.

Matrix metalloproteinase (MMP) inhibition has been associated with several activities including inhibition of TNFα [Mohler, et al., *Nature*, 370, 218–220 (1994)] and inhibition of angiogenesis. MMPs are a family of secreted and membrane-bound zinc endopeptidases that play a key role in both physiological and pathological tissue degradation [Yu, et al., *Drugs & Aging*, 1997, (3):229–244; Wojtowicz-Praga, et al., *Int. New Drugs*, 16:61–75 (1997)]. These enzymes are capable of degrading the components of the extracellular matrix, including fibrillar and non-fibrillar collagens, fibronectin, laminin, and membrane glycoproteins. Ordinarily, there is a delicate balance between cell division, matrix synthesis, matrix degradation (under the control of cytokines), growth factors, and cell matrix interactions. Under pathological conditions, however, this balance can be disrupted. Conditions and diseases associated with undesired MMP levels include, but are not limited to: tumor metastasis invasion and growth, angiogenesis, rheumatoid arthritis, osteoarthritis, osteopenias such as osteoporosis, periodontitis, gingivitis, Crohn's disease, inflammatory bowel disease, and corneal epidermal or gastric ulceration.

Increased MMP activity has been detected in a wide range of cancers [Denis, et al., Invest. *New Drugs*, 15: 175–185 (1987)]. As with TNFα, MMPs are believed to be involved in the invasive processes of angiogenesis and tumor metastasis.

DETAILED DESCRIPTION

The present invention is based on the discovery that certain classes of non-polypeptide compounds more fully described herein decrease the levels of TNFα, and/or inhibit PDEs particularly PDE 4, and/or inhibit angiogenesis and/or are useful in the treatment of cancer, inflammatory and autoimmune diseases. For example, compounds that selectively inhibit PDE 4 specifically would at least partially inhibit inflammation and relaxation of airway smooth muscle with a minimum of unwanted side effects, such as cardiovascular or anti-platelet effects. The compounds of the present invention are useful in the inhibition of phosphodiesterases, particularly PDE 4, and in the treatment of disease states mediated thereby.

The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, sepsis, endotoxic shock, graft versus host disease, wasting, inflammatory bowel disease Crohn's disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

In particular, the invention pertains to (a) 1,3,4-oxadiazole compounds of Formula I:

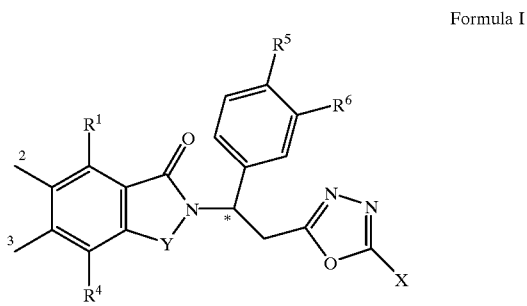

Formula I in which:
the carbon atom designated * constitutes a center of chirality;
Y is C=O, $CH_2$, $SO_2$ or $CH_2C$=O;
X is hydrogen, or alkyl of 1 to 4 carbon atoms;
each of $R^1$, $R^2$, $R^3$, and $R^4$, independently of the others, is hydrogen, halo, trifluoromethyl, acetyl, alkyl of 1 to 6 carbon atoms, alkoxy of 1 to 4 carbon atoms, nitro, cyano, hydroxy, —$CH_2NR^8R^9$, —$(CH_2)_2NR^8R^9$, or —$NR^8R^9$; or
any two of $R^1$, $R^2$, $R^3$, and $R^4$ on adjacent carbon atoms, together with the depicted benzene ring are naphthylidene, quinoline, quinoxaline, benzimidazole, benzodioxole or 2-hydroxybenzimidazole;
each of $R^5$ and $R^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;
each of $R^8$ and $R^9$ taken independently of the other is hydrogen, straight or branched alkyl of 1 to 8 carbon atoms, phenyl, benzyl, pyridyl, pyridylmethyl, or one of $R^8$ and $R^9$ is hydrogen and the other is —$COR^{10}$, or —$SO_2R^{10}$, or $R^8$ and $R^9$ taken together are tetramethylene, pentamethylene, hexamethylene, —CH=NCH=CH—, or —$CH_2CH_2X^1CH_2CH_2$— in which $X^1$ is —O—, —S—, or —NH—;
$R^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, $NR^{11}R^{12}$, $CH_2R^{14}R^{15}$, or $NR^{11}R^{12}$
wherein $R^{14}$ and $R^{15}$, independently of each other, are hydrogen, methyl, ethyl, or propyl, and
wherein $R^{11}$ and $R^{12}$, independently of each other, are hydrogen, alkyl of 1 to 8 carbon atoms, phenyl, or benzyl; and
(b) the acid addition salts of said compounds which contain a nitrogen atom susceptible of protonation.

It will be appreciated that while for convenience the compounds of Formula I are identified as 1,3,4-oxadiazoles.

The term alkyl denotes a univalent saturated or unsaturated branched, or straight, cyclic or mixture thereof hydrocarbon chain containing from 1 to 8 carbon atoms. Representative of such alkyl groups are methyl, ethyl, propyl, isopropyl, butyl, isobutyl, sec-butyl, tert-butyl, cyclopentyl, and cyclopropylmethyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, tert-butoxy, cyclohexylmethoxy, and cyclopentyimethoxy.

The term cycloalkyl as used herein denotes a univalent cyclic hydrocarbon chain which may be saturated or unsaturated. Unless otherwise stated, such chains can contain up to 18 carbon atoms and include monocycloalkyl, dicycloalkyl, polycycloalkyl, and benzocycloalkyl structures. Monocycloalkyl refers to groups having a single ring group. Polycycloalkyl denotes hydrocarbon systems containing two or more ring systems with one or more ring carbon atoms in common; ie., a spiro, fused, or bridged structure. Benzocycloalkyl signifies a monocyclic alkyl group fused to a benzo group. Representative of monocycloalkyl groups are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Representative of polycycloalkyl include decahydronaphthalene, spiro[4.5]decyl, bicyclo[2.2.1]heptyl, bicyclo[3.2.1 ]octyl, pinanyl, norbornyl, and bicyclo[2.2.2]octyl. Benzocycloalkyl is typified by tetrahydronaphthyl, indanyl, and 1.2-benzocycloheptanyl. Cycloalkoxy refers to a cycloalkyl group as just described, that is a monocycloalkyl, polycycloalkyl, or benzocycloalkyl structure, bound to the remainder of the molecule through an ethereal oxygen atom.

A first preferred group of compounds are those of Formula I in which Y is C=O.

A further preferred group of compounds are those of Formula I in which Y is $CH_2$.

A further preferred group of compounds are those of Formula I in which each of $R^1, R^2, R^3$, and $R^4$ independently of the others, is hydrogen, halo, methyl, ethyl, methoxy, ethoxy, nitro, cyano, hydroxy, or —$NR^8R^9$ in which each of $R^8$ and $R^9$ taken independently of the other is hydrogen or methyl or one of $R^8$ and $R^9$ is hydrogen and the other is —$COCH_3$, or COR, where R is alkyl, benzyl, pyridyl, or pyridylmethyl.

A further preferred group of compounds are those of Formula I in which one of $R^1$, $R^2$, $R^3$ and $R^4$ is —$NH_2$ or —$CH_3$ and the remaining of $R^1$, $R^2$, $R^3$ and $R^4$ are hydroge A further preferred group of compounds are those of Formula I in which one of $R^1$, $R^2$, $R^3$, and $R^4$ is —$NHCOCH_3$, $NHSO_2R^{10}$, or $NHCOR^{10}$, and the remaining of $R^1$, $R^2$, $R^3$ and $R^4$ are hydrogen.

A further preferred group of compounds are those of Formula I in which one of $R^1, R^2, R^3$, and $R^4$ is —$N(CH_3)_2$ and the remaining of $R^1$, $R^2$, $R^3$ and $R^4$ are hydrogen.

A further preferred group of compounds are those of Formula I in which one of $R^1, R^2, R^3$, and $R^4$ is methyl or ethyl and the remaining of $R^1, R^2, R^3$, and $R^4$ are hydrogen.

A further preferred group of compounds are those of Formula I in which each of $R^5$ and $R^6$, independently of the other, is methoxy, ethoxy, propoxy, cyclopentoxy, or cyclohexoxy.

A further preferred group of compounds are those of Formula I in which $R^5$ is methoxy and $R^6$ is alkoxy, monocycloalkoxy, polycycloalkoxy, and benzocycloalkoxy.

A further preferred group of compounds are those of Formula I in which $R^5$ is methoxy and $R^6$ is ethoxy or cyclopentoxy.

The compounds of Formula I are used, under the supervision of qualified professionals, to inhibit the undesirable effects of TNFα and PDE 4. The compounds may also be given to treat cancer conditions, undesirable angiogenesis, inflammation, skin conditions, etc. The compounds can be administered orally, rectally, or parenterally, alone or in combination with other therapeutic agents including antibiotics, steroids, etc., to a mammal in need of treatment. Use of the terms PDE IV and PDE 4 are deemed equivalent.

The compounds can also be used topically in the treatment or prophylaxis of topical disease states including, but not limited to atopic dermatitis, psoriasis, lupus, viral infections, such as those caused by the herpes viruses, or viral conjunctivitis, psoriasis, cancer, etc. PDE 4 inhibition is a preferred embodiment, though inhibition of other phosphodiesterases is envisioned.

The compounds also can be used in the veterinary treatment of mammals other than humans in need of prevention or inhibition of TNFα production or PDE 4 inhibition. TNFα mediated diseases for treatment, therapeutically or prophylactically, in animals which include disease states such as those noted above. Viral infection examples include feline immunodeficiency virus, equine infectious anemia virus, caprine arthritis virus, visna virus, and maedi virus, as well as other lentiviruses.

Methods of preparation of acids (I) are described in U.S. Pat. No. 5,605,914 which is incorporated by reference herein. The preparation of the oxadiazoles (III) can be done in a two-step fashion or in a single-pot fashion. Reaction of acid (I) with carbonyldiimidazole (CDI) or another activating agent, followed by addition of an acyl hydrazide ($NH_2NHCXO$, wherein X is a hydrogen or alkyl) provides a compound of Formula (II). Preferred solvents for this reaction ("a") are aprotic polar solvent that include acetonitrile ($CH_3CN$), tetrahydrofuran (THF), and ethyl acetate (EtOAc). Compounds of Formula (II) can be isolated at this point. Alternatively, a compound of Formula (II) can be used in the next reaction "b" without isolation (a preferred solvent is then acetonitrile). In reaction "b" dehydration of a compound of Formula (II) with dehydrating reagents such as phosphorous oxychloride ($POCl_3$) or phosphorous pentoxide ($P_2O_5$) provides a compound of Formula (III). Heat may be used in reaction "b".

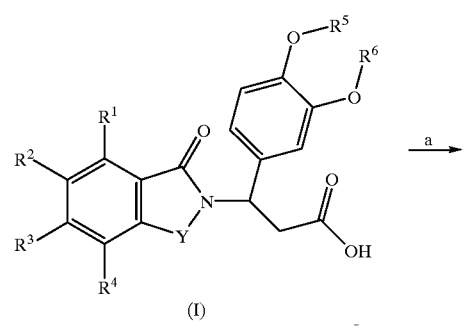

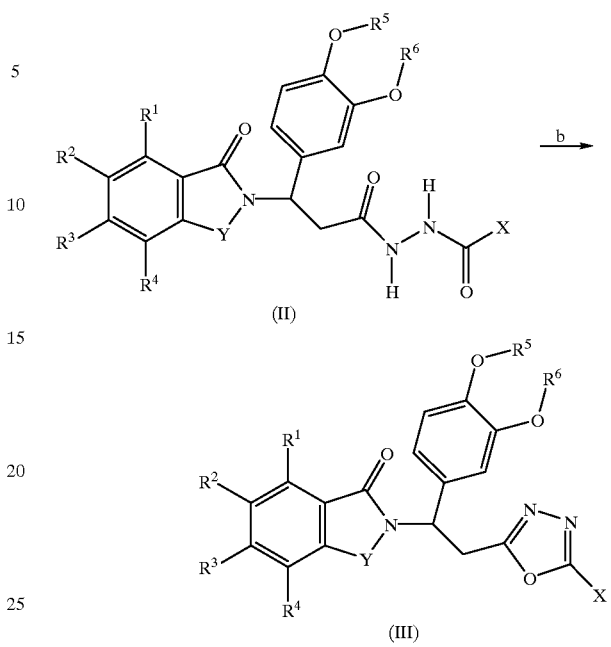

When one of $R^1$, $R^2$, $R^3$, and $R^4$ is to be amino in the final 1,3,4-oxadiazole, it often is desirable to utilize the corresponding nitro compound (I) and then reduce the resulting nitroisoindolinone to an aminoisoindolinone after formation. Alternatively, amino groups and other groups which may react can be converted to an appropriately protected group.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. 1, Schröder and Lubke, Academic Press, London and New York, 1965; "Methoden der organischen Chemie", Houben-Weyl, 4th Edition, Vol. 15/1, Georg Thieme Verlag, Stuttgart 1974, the disclosures of which are incorporated herein by reference.

The compounds of Formula I possess a center of chirality and thus can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid or base, or have such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

Preferred examples include substantially chirally pure (R)-isomer, a substantially chirally pure (S)-isomer, or a mixture thereof, wherein the isomer is 2-[1-(3-ethoxy-4-methoxyphenyl)-2-(1,3,4-oxadiazol-2-yl)ethyl]isoindoline-1,3-dione, 2-[1-(3-ethoxy-4-methoxyphenyl)-2-(1,3,4-oxadiazol-2-yl)ethyl]benzo[e]isoindoline-1,3-dione, 2-[1-(3-ethoxy-4-methoxyphenyl)-2-(1,3,4-oxadiazol-2-yl)ethyl]-4-methylisoindoline-1,3-dione, 2-[1-(3-ethoxy-4-methoxyphenyl)-2-(1,3,4-oxadiazol-2-yl)ethyl]-5-methylisoindoline-1,3-dione, 2-[1-(3-cyclopentyloxy-4-methoxy-phenyl)-2-(1,3,4-oxadiazol-2-yl)ethyl]-5-methylisoindoline-1,3-dione, 2-[1-(3-cyclopentyloxy-4-methoxyphenyl)-2-(1,3,4-oxadiazol-2-yl)ethyl]-4-methylisoindoline-1,3-dione, N-[2-[1-(3-cyclopentyloxy-4-methoxyphenyl)-2-(1,3,4-oxadiazol-2-yl)ethyl]-1,3-dioxoisoindolin-4-yl]-acetamide, N-[2-[1-(3-ethoxy-4-methoxyphenyl)-2-(1,3,4-oxadiazol-2-yl)ethyl]-1,3-dioxoisoindolin-4-yl]-acetamide, 5-(tert-butyl)-2-[1-(3-ethoxy-4-methoxyphenyl)-2-(1,3,4-oxadiazol-2-yl)ethyl]isoindoline-1,3-dione, 2-[1-(3,4-dimethoxyphenyl)-2-(1,3,4-oxadiazol-2-yl)ethyl]isoindoline-1,3-dione, 2-[1-(3-ethoxy-4-methoxyphenyl)-2-(1,3,4-oxadiazol-2-yl)ethyl]isoindolin-1-one, 2-[1-(3-ethoxy-4-methoxyphenyl)-2-(5-methyl(1,3,4-oxadiazol-2-yl))ethyl]isoindolin-1-one, and 2-[1-(3-ethoxy-4-methoxyphenyl)-2-(1,3,4-oxadiazol-2-yl)ethyl]-3-pyrrolino[3,4-]quinoline-1,3-dione.

The present invention also pertains to the physiologically acceptable non-toxic acid addition salts of the compounds of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Oral dosage forms include tablets, capsules, dragees, and similar shaped, compressed pharmaceutical forms containing from 1 to 100 mg of drug per unit dosage. Mixtures containing from 20 to 100 mg/mL can be formulated for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of the present invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone polyvinylpyrrolidone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

The following examples will serve to further typify the nature of this invention but should not be construed as a limitation in the scope thereof, which scope is defined solely by the appended claims.

EXAMPLE 1

2-[1-(3-Ethoxy-4-methoxyphenyl)-2-(1,3,4-oxadiazol-2-yl)ethyl]isoindoline-1,3-dione A mixture of 3-(1,3-dioxoisoindolin-2-yl)-3-(3-ethoxy-4-methoxyphenyl)propanoic acid (3.0 g, 8.1 mmol) and carbonyldiimidazole (1.45 g, 8.94 mmol) in tetrahydrofuran (15 mL) was stirred at room temperature for 2 hours. To the solution was added formic hydrazide (644 mg, 10.7 mmol). The mixture was stirred for 18 hours. The resulting suspension was filtered and washed with ether. The isolated solid was stirred in a mixture of ethyl acetate (40 mL) and water (10 mL) for 1 hour. The suspension was filtered and washed with water and ether to give crude 3-(1,3-dioxoisoindolin-2-yl)-N-carbonylamino-3-(3-ethoxy-4-methoxyphenyl) propanamide (1.3 g, 39% yield). A solution of 3-(1,3-dioxoisoindolin-2-yl)-N-carbonylamino-3-(3-ethoxy-4-methoxyphenyl)propanamide (600 mg, 1.46 mmol) and phosphorus oxychloride ($POCl_3$, 0.54 mL, 5.8 mmol) in acetonitrile (20 mL) was heated to reflux for 2 hours. This solution was poured into water (10 mL). The aqueous layer was extracted with ethyl acetate (2×50 mL). The combined organic layers were washed with sodium hydrogen carbonate (50 mL, sat), brine (50 mL) and dried over magnesium sulfate. Removal of solvent and chromatography gave an oil. The oil was slurried in ether (10 mL). The resulting suspension was filtered to yield 2-[1-(3-ethoxy-4-methoxyphenyl)-2-(1,3,4-oxadiazol-2-yl)ethyl]isoindoline-1,3-dione as a white solid (250 mg, 43% yield): mp, 132.0–134.0° C.; $^1$H NMR ($CDCl_3$); δ 1.46 (t, J=6.9 Hz, 3H, $CH_3$), 2.82 (dd, J=6.0, 15.6 Hz, 1H, CHH), 3.84 (s, 3H, $CH_3$), 4.11 (q, J=7.0 Hz, 2H, $CH_2$), 4.37 (dd, J=10.3, 15.7 Hz, 1H, CHH), 5.81 (dd, J=6.0, 10.3 Hz, 1H, NCH), 6.62 (d, J=7.9 Hz, 1H, Ar), 7.13–7.17 (m, 2H, Ar), 7.67–7.72 (m, 2H, Ar), 7.75–7.62 (m, 2H, Ar), 8.29 (s, 1H, Ar); $^{13}$C NMR ($CDCl_3$)δ 14.69, 27.70, 51.85, 55.90, 64.42, 111.32, 112.51, 120.32, 123.44, 130.14, 13163, 134.13, 148.39, 143.43, 153.03, 163.99, 167.93; Anal Calcd for $C_{21}H_{29}N_3O_5$: C, 64.12; H, 4.87; N, 10.68. Found: C, 63.84; H, 4.90; N, 10.48.

EXAMPLE 2

2-[1-(3-Ethoxy-4-methoxyphenyl)-2-(1,3,4-oxadiazol-2-yl)ethyl]benzo[e]isoindoline-1,3-dione 2-[1-(3-Ethoxy-4-methoxyphenyl)-2-(1,3,4-oxadiazol-2-yl)ethyl]benzo[e]isoindoline-1,3-dione was prepared by the procedure used in Example 1. Thus, reaction of 3-(1,3-dioxobenzo[e]isoindolin-2-yl)-3-(3-ethoxy-4-methoxyphenyl)propanoic acid (1.50 g, 3.58 mmol), carbonyldiimidazole (0.70 g, 4.3 mmol) and formic hydrazide (310 mg, 5.16 mmol) in tetrahydrofuran (20 mL) gave crude 3-(1,3-dioxobenzo[e]isoindolin-2-yl)-N-carbonylamino-3-(3-ethoxy4-methoxyphenyl)propanamide (1.0 g, 2.2 mmol), which was then treated with phosphorus oxychloride ($POCl_3$, 0.4 mL, 4.3 mmol) in acetonitrile (10 mL). The product was obtained as a yellow solid (135 mg, 8% overall yield): mp, 139.0–141.5° C.; $^1$H NMR ($CDCl_3$) δ 1.47 (t, J=7.2 Hz, 3H, $CH_3$), 3.85 (s, 3H, $CH_3$), 3.87 (dd, J=6.0, 15.6 Hz, 1H, CHH), 4.13 (q, J=6.9 Hz, 2H, $CH_2$), 4.42 (dd, J=10.2, 15.6 Hz, 1H, CHH), 5.87 (t, J=5.9, 10.4 Hz, 1H, NCH), 6.84 (d, J=8.7 Hz, 1H, Ar), 7.18–7.27 (m, 2H, Ar), 7.64–7.75 (m, 2H, Ar), 7.81 (d, J=8.3 Hz, 1H, Ar), 7.94 (d, J=7.6 Hz, 1H, Ar), 8.14 (d, J=8.2 Hz, 1H, Ar), 8.29 (s, 1H, CH), 8.90 (d, J=7.5 Hz, 1H, Ar); $^{13}$C NMR ($CDCl_3$) δ 14.63, 27.79, 51.69, 55.84, 64.39, 111.34, 112.53, 118.41, 121.22, 124.83, 126.88, 127.93, 128.62, 128.74, 129.44, 130.31, 130.87, 135.06, 136.59, 148.37, 149.36, 152.95, 164.04, 168.51, 169.07; Anal Calcd for $C_{25}H_{21}N_3O_5$: C, 67.71; H, 4.77; N, 9.48. Found: C, 67.80; H, 4.95; N, 9.20.

EXAMPLE 3

2-[1-(3-Ethoxy-4-methoxyphenyl)-2-(1,3,4-oxadiazol-2-yl)ethyl]-4-methylisoindoline-1,3-dione 2-[1-(3-Ethoxy-4-methoxyphenyl)-2-(1,3,4-oxadiazol-2-yl)ethyl]-4-methylisoindoline-1,3-dione was prepared by the procedure of Example 1. Reaction of 3-(3-ethoxy-4-methoxyphenyl)-3-(4-methyl-1,3-dioxoisoindolin-2-yl)propanoic acid (2.03 g, 5.29 mmol), carbonyldiimidazole (1.03 g, 6.35 mmol) and formic hydrazide (420 mg, 6.99 mmol) in tetrahydrofuran (20 mL) gave crude N-carbonylamino-3-(3-ethoxy-4-methoxyphenyl)-3-(4-methyl-1,3-dioxoisoindolin-2-yl)propanamide(610 mg, 1.43 mmol), which was then treated with phosphorus oxychloride (0.4 mL, 4.3 mmol) in acetonitrile (6 mL). The product was obtained as a white solid (311 mg, 14% overall yield): mp, 96.0–98.0° C.; $^1$H NMR ($CDCl_3$) δ 1.47 (t, J=6.9 Hz, 3H, $CH_3$), 2.67 (s, 3H, $CH_3$), 3.81 (dd, J=6.0, 15.7 Hz, 1H, CHH), 3.85 (s, 3H, $CH_3$), 4.12 (q, J=6.9 Hz, 2H, $CH_2$), 4.37 (dd, J=10.2, 15.6 Hz, 1H, CHH), 5.81 (t, J=6.0, 10.3 Hz, 1H, NCH), 6.83 (d, J=8.7 Hz, 1H, Ar), 7.14–7.17 (m, 2H, Ar), 7.43 (d, J=7.6 Hz, 1H, Ar), 7.54 (t, J=7.3 H, Ar), 7.63 (d, J=7.1 Hz, 1H, Ar), 8.30 (s, 1H, CH); $^{13}$C NMR ($CDCl_3$) δ 14.69, 17.52, 27.71, 51.62, 55.92, 64.46, 111.37, 112.63, 120.33, 121.06, 128.31, 130.33, 132.07, 133.59, 136.55, 138.18, 148.39, 149.42, 153.02, 164.08, 168.04, 168.53; Anal Calcd for $C_{22}H_{21}N_3O_5$+0.2 $H_2O$: C, 64.29; H, 5.25; N, 10.22; $H_2O$, 0.90. Found: C, 64.62; H, 5.30; N, 9.83; $H_2O$, 0.71.

EXAMPLE 4

2-[1-(3-Ethoxy-4-methoxyphenyl)-2-(1,3,4-oxadiazol-2-yl)ethyl]-5-methylisoindoline-1,3-dione 2-[1-(3-Ethoxy-4-methoxyphenyl)-2-(1,3,4-oxadiazol-2-yl)ethyl]-5-methylisoindoline-1,3-dione was prepared by the procedure of Example 1. Reaction of 3-(3-ethoxy-4-methoxyphenyl)-3-(5-methyl-1,3-dioxoisoindolin-2-yl)propanoic acid (1.81 g, 4.72 mmol), carbonyldiimidazole (0.92 g, 5.7 mmol) and formic hydrazide (375 mg, 6.2 mmol) in ethyl acetate (20 mL) gave crude N-carbonylamino-3-(3-ethoxy-4-methoxyphenyl)-3-(5-methyl-1,3-dioxoisoindolin-2-yl)propanamide (0.93 g, 2.2 mmol), which was then treated with phosphorus oxychloride (0.4 mL, 4.3 mmol) in acetonitrile (12 mL). The product was obtained as a white solid (371 mg, 19% overall yield): mp, 122.0–124.0° C.; $^1$H NMR ($CDCl_3$) δ 1.45 (t, J=6.9 Hz, 3H, $CH_3$), 2.48 (s, 3H, $CH_3$), 3.80 (dd, J=6.0, 15.6 Hz, 1H, CHH), 3.84 (s, 3H, $CH_3$), 4.10 (q, J=6.9 Hz, 2H, $CH_2$), 4.35 (dd, J=10.3, 15.6 Hz, 1H, CHH), 5.79 (dd, J=6.0, 10.2 Hz, 1H, NCH), 6.82 (d, J=8.1 Hz, 1H, Ar), 7.12–7.17 (m, 2H, Ar), 7.47 (d, J=7.5 Hz, 1H, Ar), 7.59 (s, 1H, Ar), 7.68 (d, J=7.6 Hz, 1H, Ar), 8.28 (s, 1H, Ar); $^{13}$C NMR ($CDCl_3$) δ 14.61, 21.86, 27.67, 51.71, 55.83, 64.36, 111.29, 112.49, 120.22, 123.27, 123.88, 128.97, 130.23, 131.95, 134.58, 145.39, 148.33, 149.34, 152.93, 163.97, 167.91, 168.04; Anal Calcd for $C_{22}H_{21}N_3O_5$: C, 64.86; H, 5.20; N, 10.31. Found: C, 64.77; H, 5.07; N, 10.30.

EXAMPLE 5

2-[1-(3-Cyclopentyloxy-4-methoxyphenyl)-2-(1,3,4-oxadiazol-2-yl)ethyl]-5-methylisoindoline-1,3-dione 2-[1-(3-Cyclopentyloxy-4-methoxyphenyl)-2-(1,3,4-oxadiazol-2-yl)ethyl]-5-methylisoindoline-1,3-dione was prepared by the procedure of Example 1. Reaction of 3-(3-cyclopentyloxy-4-methoxyphenyl)-3-(5-methyl-1,3-dioxoisoindolin-2-yl)propanoic acid (2.33 g, 5.5 mmol), carbonyldiimidazole (1.07 g, 6.59 mmol) and formic hydrazide (436 mg, 7.26 mmol) in ethyl acetate (20 mL) gave crude N-carbonylamino-3-(3-cyclopentyloxy-4-methoxyphenyl)-3-(5-methyl-1,3-dioxoisoindolin-2-yl)propanamide (2.24 g, 4.8 mmol), which was then treated with phosphorus oxychloride (0.9 mL, 9.6 mmol) in acetonitrile (10 mL). The product was obtained as a white solid (728 mg, 32% overall yield): mp, 184.0–186.5° C.; $^1$H NMR ($CDCl_3$) δ 1.55–2.00 (m, 8H, $C_5H_8$), 2.48 (s, 3H, $CH_3$), 3.81 (s, 3H, $CH_3$), 3.82 (dd, J=6.1, 15.7 Hz, 1H, CHH), 4.36 (dd, J=10.3, 15.7 Hz, 1H, CHH), 4.74–4.81 (m, 1H, OCH), 5.79 (dd, J=5.9, 10.3 Hz, 1H, NCH), 6.80 (d, J=8.4 Hz, 1H, Ar), 7.10 (dd, J=2.0, 8.3 Hz, 1H, Ar), 7.18 (d, J=2.0 Hz, 1H, Ar), 7.47 (d, J=7.5 Hz, 1H, Ar), 7.59 (s, 1H, Ar), 7.67 (d, J=7.6 Hz, 1H, Ar), 8.28 (s, 1H, CH); $^{13}$C NMR ($CDCl_3$) δ 21.95, 24.09, 27.75, 32.77, 51.79, 56.00, 80.48, 111.73, 114.51, 120.16, 123.34, 123.95, 129.05, 130.22, 132.03, 134.65, 145.44, 147.75, 150.03, 153.00, 164.08, 167.98, 168.11; Anal Calcd for $C_{25}H_{25}N_3O_5$+0.13 $Et_2O$: C, 67.05; H, 5.80; N, 9.19. Found: C, 66.95; H, 5.88; N, 8.97. (HNMR showed the sample contained 0.13 equiv. of ether).

EXAMPLE 6

2-[1-(3-Cyclopentyloxy-4-methoxyphenyl)-2-(1,3,4-oxadiazol-2-yl)ethyl]-4-methylisoindoline-1,3-dione 2-[1-(3-Cyclopentyloxy-4-methoxyphenyl)-2-(1,3,4-oxadiazol-2-yl)ethyl]-4-methylisoindoline-1,3-dione was prepared by the procedure of Example 1. Reaction of 3-(3-cyclopentyloxy-4-methoxyphenyl)-3-(4-methyl-1,3-dioxoisoindolin-2-yl)propanoic acid (2.23 g, 5.27 mmol), carbonyldiimidazole (0.94 g, 5.8 mmol) and formic hydrazide (382 mg, 6.36 mmol) in ethyl acetate (20 mL) gave crude N-carbonylamino-3-(3-cyclopentyloxy-4-methoxyphenyl)-3-(4-methyl-1,3-dioxoisoindolin-2-yl)propanamide (1.71 g, 3.67 mmol), which was then treated with phosphorus oxychloride (0.8 mL, 8.6 mmol) in acetonitrile (10 mL). The product was obtained as a white solid (368 mg, 16% overall yield): mp, 126.0–128.5° C.; $^1$H NMR ($CDCl_3$) δ 1.21–1.99 (m, 8H, $C_5H_8$), 2.66 (s, 3H, $CH_3$), 3.81 (s, 3H, $CH_3$), 3.82 (dd, J=6.1, 15.8 Hz, 1H, CHH), 4.37 (dd, J=10.3, 15.6 Hz,1H, CHH), 4.76–4.83 (m,1H, OCH), 5.80

(dd, J=5.9, 10.3 Hz, 1H, NCH), 6.81 (d, J=8.4 Hz, 1H, Ar), 7.09–7.18 (m, 2H, Ar), 7.43 (d, J=7.6 Hz, 1H, Ar), 7.54 (t, J=7.4 Hz, 1H, Ar), 7.62 (d, J=7.1 Hz, 1H, Ar), 8.29 (s, 1H, CH); $^{13}$C NMR (CDCl$_3$) δ 17.45, 24.00, 27.67, 32.68, 51.57, 55.94, 80.44, 111.69, 114.55, 120.13, 120.98, 128.25, 130.22, 132.01, 133.50, 136.44, 138.08, 147.68, 149.99, 152.93, 164.04, 167.95, 168.56; Anal Calcd for C$_{25}$H$_{25}$N$_3$O$_5$: C, 67.10; H, 5.63; N, 9.39. Found: C, 67.14; H, 5.55; N, 9.19.

EXAMPLE 7

N-[2-[1-(3-Cyclopentyloxy-4-methoxyphenyl)-2-(1,3,4-oxadiazol-2-yl)ethyl]-1,3-dioxoisoindolin-4-yl]acetamide N-[2-[1-(3-Cyclopentyloxy-4-methoxyphenyl)-2-(1,3,4-oxadiazol-2-yl)ethyl]-1,3-dioxoisoindolin-4-yl]acetamide was prepared by the procedure of Example 1. Reaction of 3-[4-(acetylamino)-1,3-dioxoisoindolin-2-yl]-3-(3-cyclopentyloxy-4-methoxyphenyl)propanoic acid (2.0 g, 4.3 mmol), carbonyidiimidazole (0.77 g, 4.8 mmol) and formic hydrazide (314 mg, 4.7 mmol) in ethyl acetate (20 mL) gave crude 3-[4-(acetylamino)-1,3-dioxoisoindolin-2-yl]-N-carbonylamino-3-(3-cyclopentyloxy-4-methoxyphenyl)propanamide, which was then reacted with phosphorus oxychloride (1.0 mL, 10.7 mmol) in acetonitrile (15 mL). The product was isolated as a yellow solid (555 mg, 28% overall yield): mp, 115.0–117.0° C.; $^1$H NMR (CDCl$_3$) δ 1.62–1.97 (m, 8H, C$_5$H$_8$), 2.27 (s, 3H, CH$_3$), 3.76 (dd, J=5.6, 15.9 Hz, 1H, CHH), 3.83 (s, 3H, CH$_3$), 4.40 (dd, J=10.7, 15.8 Hz, 1H, CHH), 4.76–4.82 (m, 1H, OCH), 5.78 (dd, J=5.5, 10.7 Hz, 1H, NCH), 6.84 (d, J=8.1 Hz, 1H, Ar), 7.09–7.15 (m, 2H, Ar), 7.47 (d, J=7.2 Hz, 1H, Ar), 7.65 (t, J=7.5 Hz, 1H, Ar), 8.32 (s, 1H, CH), 8.76 (d, J=8.4 Hz, 1H, Ar), 9.48 (s, 1H, NH); $^{13}$C NMR (CDCl$_3$) δ 23.99, 24.85, 27.58, 32.68, 51.71, 55.95, 80.53, 111.75, 114.46, 115.10, 118.03, 119.88, 124.82, 129.77, 130.95, 135.94, 137.48, 147.77, 150.21, 152.99, 163.85, 167.36, 169.07, 167.71; Anal Calcd for C$_{26}$H$_{26}$N$_4$O$_6$+0.1 hexane: C, 64.01; H, 5.53; N, 11.22. Found: C, 64.01; H, 5.58; N, 10.97. (HNMR showed the product contained 10% of hexane).

EXAMPLE 8

N-[2-[1-(3-Ethoxy-4-methoxyphenyl)-2-(1,3,4-oxadiazol-2-yl)ethyl]-1,3-dioxoisoindolin-4-yl]acetamide A mixture of 3-[4-(acetylamino)-1,3-dioxoisoindolin-2-yl]-3-(3-ethoxy-4-methoxyphenyl)propanoic acid (1.69 g, 3.96 mmol) and carbonyidiimidazole (0.71 g, 4.4 mmol) in acetonitrile (20 mL) was stirred at room temperature for 2 hours. To the solution was added formic hydrazide (289 mg, 4.81 mmol). The mixture was then stirred for 18 hours. To the resulting solution was added phosphorus oxychloride (1.0 mL, 10.7 mmol), and this mixture was heated at reflux for 2 hours. The solution was poured to water (10 mL). The aqueous layer was extracted with ethyl acetate (2×50 mL). The combined organic layers were washed with aqueous sodium hydrogen carbonate (50 mL, sat), brine (50 mL) and then dried over magnesium sulfate. Chromatography followed by removal of solvent yielded an oil. The oil was stirred in ether (10 mL) to give a suspension. This suspension was filtered to yield N-[2-[1-(3-ethoxy-4-methoxyphenyl)-2-(1,3,4-oxadiazol-2-yl)ethyl]-1,3-dioxoisoindolin-4-yl]acetamide as a white solid (478 mg, 27% yield): mp, 141.0–143.0° C.; $^1$H NMR (CDCl$_3$) δ 1.47 (t, J=6.9 Hz, 3H, CH$_3$), 2.26 (s, 3H, CH$_3$), 3.74 (dd, J=5.8, 15.8 Hz, 1H, CHH), 3.85 (s, 3H, CH$_3$), 4.11 (q, J=7.1 Hz, 2H, CH$_2$), 4.38 (dd, J=10.6, 15.8 Hz, 1H, CHH), 5.78 (dd, J=5.6, 10.6 Hz, 1H, NCH), 6.83 (d, J=8.9 Hz, 1H, Ar), 7.11–7.14 (m, 2H, Ar), 7.45 (d, J=7.2 Hz, 1H, Ar), 7.64 (d, J=7.5 Hz, 1H, Ar), 8.31 (s, 1H, Ar), 8.75 (d, J=8.4 Hz, 1H, Ar), 9.46 (br s, 1H, NH); $^{13}$C NMR (CDCl$_3$) δ 14,70, 24.92, 27.60, 51.74, 55.92, 64.50, 111.40, 112.47, 115.15, 118.11, 120.15, 124.91, 129.87, 130.99, 136.01, 137.55, 148.49, 149.59, 153.07, 163.88, 167.44, 169.14, 169.75; Anal Calcd for C$_{23}$H$_{22}$N$_4$O$_6$: C, 61.33; H, 4.92; N, 12.44. Found: C, 61.37; H, 4.88; N, 12.11.

EXAMPLE 9

5-(tert-Butyl)-2-[1-(3-ethoxy-4-methoxyphenyl)-2-(1,3,4-oxadiazol-2-yl)ethyl]isoindoline-1,3-dione 5-(t-Butyl)-2-[1-(3-ethoxy-4-methoxyphenyl)-2-(1,3,4-oxadiazol-2-yl)ethyl]isoindoline-1,3-dione was prepared as described for Example 8 from 3-[5-(tert-butyl)-1,3-dioxoisoindolin-2-yl]-3-(3-ethoxy-4-methoxyphenyl)propanoic acid (2.0 g, 4.7 mmol), carbonyldiimidazole (0.81 g, 5.0 mmol), formic hydrazide (0.35 g, 5.8 mmol), and phosphorus oxychloride (1.0 mL, 10.7 mmol) in acetonitrile (20 mL). The product was isolated as a white solid (800 mg, 38% yield): mp, 136.0–138.5° C.; $^1$H NMR (CDCl$_3$) δ 1.35 (s, 9H, CH$_3$), 1.44 (t, J=6.9 Hz, 3H, CH$_3$), 3.79 (dd, J=5.9, 16.1 Hz, 1H, CHH), 3.84 (s, 3H, CH$_3$), 4.11 (q, J=7.1 Hz, 2H, CH$_2$), 4.38 (dd, J=10.3, 15.8 Hz, 1H, CHH), 5.80 (dd, J=5.9, 10.4 Hz, 1H, NCH), 6.82 (d, J=8.2 Hz, 1H, Ar), 7.11–7.17(m, 2H, Ar), 7.70 (br s, 2H, Ar), 7.82 (br s, 1H, Ar), 8.29 (s, 1H, Ar); $^{13}$C NMR (CDC$_3$) δ 14.71, 27.73, 31.08, 35.72, 51.78, 55.92, 64.44, 111.36, 112.58, 120.31, 120.63, 123.26, 128.94, 130.33, 131.14, 131.84, 148.41, 149.42, 153.02, 158.82, 164.07, 168.25, 168.39; Anal Calcd for C$_{25}$H$_{27}$N$_3$O$_5$+0.11 H$_2$O: C, 66.51; H, 6.08; N, 9.31; H$_2$O, 0.43. Found: C, 66.42; H, 5.83; N, 9,18; H$_2$O, 0.43.

EXAMPLE 10

2-[1-(3,4-Dimethoxyphenyl)-2-(1,3,4-oxadiazol-2-yl)ethyl]isoindoline-1,3-dione 2-[1-(3,4-Dimethoxyphenyl)-2-(1,3,4-oxadiazol-2-yl)ethyl]isoindoline-1,3-dione was prepared by the procedure of Example 8 from 3-(3,4-dimethoxyphenyl)-3-(1,3-dioxoisoindolin-2-yl)propanoic acid (2.0 g, 3.6 mmol), carbonyidiimidazole (1.0 g, 6.2 mmol), formic hydrazide (0.41 g, 6.8 mmol), and phosphorus oxychloride (1.3 mL, 14 mmol) in acetonitrile (20 mL). The product was obtained as a white solid (730 mg, 34% yield): mp, 83.0–85.0° C.; $^1$H NMR (CDCl$_3$) δ 3.82 (dd, J=6.0, 16.0 Hz, 1H, CHH), 3.85 (s, 3H, CH$_3$), 3.90 (s, 3H, CH$_3$), 4.39 (dd, J=10.3, 15.7 Hz, 1H, CHH), 5.84 (dd, J=6.0, 10.3 Hz, 1H, NCH), 6.81–6.85 (m, 1H, Ar), 7.16–7.19 (m, 2H, Ar), 7.68–7.73 (m, 2H, Ar), 7.77–7.83 (m, 2H, Ar), 8.30 (s, 1H, CH); $^{13}$C NMR (CDCl$_3$) δ 27.66, 51.76, 55.79, 55.89, 111.00, 111.07, 120.29, 123.3, 8, 130.16, 131.55, 134.07, 149.03, 149.11, 152.96, 163.90, 167.86; Anal Calcd for C$_{20}$H$_{17}$N$_3$O$_6$+0.3 Et$_2$O: C, 63.22; H, 5.20; N, 10.32. Found: C, 63.40; H, 5.02; N, 10.46. ($^1$H NMR showed that the sample contained 30% of ether).

EXAMPLE 11

2-[1-(3-Ethoxy-4-methoxyphenyl)-2-(1,3,4-oxadiazol-2-yl)ethyl]isoindolin-1-one 2-[1-(3-Ethoxy-4-methoxyphenyl)-2-(1,3,4-oxadiazol-2-yl)ethyl]isoindolin-1-one was prepared as described in Example 1. Reaction of 3-(3-ethoxy-4-methoxyphenyl)-3-(1-oxoisoindolin-2-yl)propanoic acid (1.50 g, 4.22 mmol), carbonyldiimidazole (0.80 g, 4.9 mmol) and formic hydrazide (310 mg, 5.16 mmol) in tetrahydrofuran (10 mL) yielded crude N-carbonylamino-3-(3-ethoxy-4-methoxyphenyl)-3-(1-oxoisoindolin-2-yl)propanamide (1.0 g, 2.2 mmol), which was then reacted with phosphorus pentoxide (2.32 g, 16.3 mmol) in chloroform (30 mL) at room temperature for 18 hours. The product was obtained as a white solid (250 mg, 16% overall yield): mp, 143.5–144.5° C.; $^1$H NMR (CDCl$_3$); δ 1.43 (t, J=7.0 Hz, 3H, CH$_3$), 3.65 (dd, J=6.1, 15.1 Hz, 1H, CHH), 3.85 (s, 3H, CH$_3$), 3.87 (dd, J=9.9, 15.0 Hz, 1H, CHH), 4.01–4.12 (m, 3H, NCHH, CH$_2$), 4.46 (d, J=16.6 Hz, 1H, NCHH), 5.99 (dd, J=6.1, 10.1 Hz, 1H, NCH), 6.83–6.87 (m, 1H, Ar), 6.94–7.01 (m, 2H, Ar), 7.34–7.52 (m, 3H, Ar), 7.78 (d, J=7.1 Hz,1H, Ar), 8.34 (s, 1H, NCH); $^{13}$C NMR (CDCl$_3$) δ 14.60, 27.84, 46.19, 52.13, 55.86, 64.45, 111.32, 112.45, 118.98, 122.78, 123.72, 127.95, 129.95, 131.49, 131.98, 141.09, 148.66, 149.35, 153.31, 163.86, 168.25; Anal Calcd for C$_{21}$H$_{21}$N$_3$O$_4$+0.06 CH$_2$Cl$_2$: C, 65.79; H, 5.54; N, 10.93. Found: C, 65.87; H, 5.67; N, 10.89.

EXAMPLE 12

2-[1-(3-Ethoxy-4-methoxyphenyl)-2-(5-methyl(1,3,4-oxadiazol-2-yl))ethyl]isoindolin-1-one 2-[1-(3-Ethoxy-4-methoxyphenyl)-2-(5-methyl(1,3,4-oxadiazol-2-yl))ethyl]isoindolin-1-one was prepared by the procedure of Example 1. Reaction 3-(3-ethoxy-4-methoxyphenyl)-3-(1-oxoisoindolin-2-yl)propanoic acid (1.50 g, 4.22 mmol), carbonyldiimidazole (0.76 g, 4.7 mmol) and acetic hydrazide (381 mg, 5.16 mmol) in tetrahydrofuran (15 mL) gave crude N-carbonylamino-3-(3-ethoxy-4-methoxyphenyl)-3-(1-oxoisoindolin-2-yl) propanamide (1.22 9, 3.06 mmol), which (650 mg, 1.47 mmol) was then reacted with phosphorus pentoxide (2.0 g, 14 mmol) in chloroform (30 mL) at room temperature for 18 hours The product was obtained as a white solid (250 mg, 32% overall yield): mp, 125.5–128.0° C.; $^1$H NMR (CDCl$_3$); δ 1.43 (t, J=7.0 Hz, 3H, CH$_3$), 2.46 (s, 3H, CH$_3$), 3.56 (dd, J=6.3, 15.1 Hz, 1H, CHH), 3.76 (dd, J=10.0, 15.0 Hz, 1H, CHH), 3.86 (s, 3H, CH$_3$), 4.02–4.11 (m, 3H, NCHH, CH$_2$), 4.46 (d, J=16.6 Hz, 1H, NCHH), 5.97 (dd, J=6.3, 9.9 Hz, 1H, NCH), 6.83–6.87 (m, 1H, Ar), 6.95–7.01 (m, 2H, Ar), 7.35–7.53 (m, 3H, Ar), 7.77–7.81 (m, 1H, Ar); $^{13}$C NMR (CDCl$_3$) δ 10.89, 14.64, 28.04, 46.18, 52.08, 55.89, 64.47, 111.32, 112.51, 119.03, 122.81, 123.74, 127.95, 130.13, 131.48, 132.11, 141.17, 148.64, 149.31, 163.86, 164.23, 168.30; Anal Calcd for C$_{22}$H$_{23}$N$_3$O$_4$+0.28 EtOAc: C, 66.42; H, 6.08; N, 10.05. Found: C, 66.47; H, 5.98; N, 10.04. ($^1$H NMR showed that the sample contained 28% of ethyl acetate).

EXAMPLE 13

2-[1-(3-Ethoxy-4-methoxyphenyl)-2-(1,3,4-oxadiazol-2-yl)ethyl]-3-pyrrolino[3,4]quinoline-1,3-dione 2-[1-(3-Ethoxy-4-methoxyphenyl)-2-(1,3,4-oxadiazol-2-yl)ethyl]-3-pyrrolino[3,4-h]-quinoline-1,3-dione was prepared by the procedure of Example 1. Reaction of 3-(1,3-dioxo(3-pyrrolino[3,4-h]quinolin-2-yl))-3-(3-ethoxy-4-methoxyphenyl)propanoic acid (1.0 g, 2.4 mmol), CDI (0.46 g, 2.8 mmol) and formic hydrazide (0.20 g, 3.4 mmol) in THF (10 mL) gave crude 3-(1,3-dioxo(3-pyrrolino[3,4-h] quinolin-2-yl))-N-carbonylamino-3-(3-ethoxy-4-methoxyphenyl)propanamide (1.12 g), which was then reacted with phosphorus oxychloride (0.8 mL, 8.6 mmol) in acetonitrile (30 mL). The product was obtained as a white solid (350 mg, 33% overall yield): mp, 166–168° C.; $^1$H NMR (CDCl$_3$) δ 1.47 (t, J=6.8 Hz, 3H, CH$_3$), 3.85 (dd, J=5.9, 15.8 Hz, 1H, CHH), 3.85 (s, 3H, CH$_3$), 4.13 (q, J=6.9 Hz, 2H, CH$_2$), 4.48 (dd, J=10.4, 15.8 Hz, 1H, CHH), 5.91 (dd, J=5.8, 10.4 Hz, 1H, NCH), 6.82–6.85 (m, 1H, Ar), 7.21–7.25 (m, 2H, Ar), 7.58 (dd, J=4.2, 8.4 Hz, 1H, Ar), 7.94 (d, J=8.0 Hz, 1H, Ar), 8.19 (d, J=8.2 Hz, 1H, Ar), 8.27 (dd, J=1.7, 8.4 Hz, 1H, Ar), 8.28 (s, 1H, CH), 9.24 (dd, J=1.7, 4.2 Hz, 1H); $^{13}$C NMR (CDCl$_3$) δ 14.63, 27.60, 51.83, 55.85, 64.39, 111.29, 112.58, 119.52, 120.43, 123.16, 126.81, 130.08, 132.14, 134.44, 135.57, 136.68, 142.77, 148.34, 149.36, 152.97, 154.27, 163.99, 167.07, 167.80, Anal Calcd for C$_{24}$H$_{20}$N$_4$O$_5$+0.05 CH$_2$Cl$_2$: C, 64.38; H, 4.52; N, 12.49. Found: C, 64.33; H, 4.58; N, 12.12. (H NMR showed the sample contained ~5% of CH$_2$Cl$_2$).

EXAMPLE 14

Tablets, each containing 50 mg of 2-[1-(3-cyclopentyloxy-4-methoxyphenyl)-2-(1,3,4-oxadiazol-2-yl)ethyl]-5-methylisoindoline-1,3-dione are prepared in the following manner:

| Constituents (for 1000 tablets) | |
|---|---|
| 2-[1-(3-cyclopentyloxy-4-methoxyphenyl)-2-(1,3,4-oxadiazol-2-yl)ethyl]-5-methylisoindoline-1,3-dione | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 15

Tablets, each containing 100 mg of 2-[1-(3-cyclopentyloxy-4-methoxyphenyl)-2-(1,3,4-oxadiazol-2-yl)ethyl]-5-methylisoindoline-1,3-dione, can be prepared in the following manner:

| Constituents (for 1000 tablets) | |
|---|---|
| 2-[1-(3-cyclopentyloxy-4-methoxyphenyl)-2-(1,3,4-oxadiazol-2-yl)ethyl]-5-methylisoindoline-1,3-dione | 100.0 g |
| lactose | 100.0 g |

-continued

| Constituents (for 1000 tablets) | |
|---|---|
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 16

Tablets for chewing, each containing 75 mg of 2-[1-(3-cyclopentyloxy-4-methoxyphenyl)-2-(1,3,4-oxadiazol-2-yl)ethyl]-5-methylisoindoline-1,3-dione, can be prepared in the following manner:

| Composition (for 1000 tablets) | |
|---|---|
| 2-[1-(3-cyclopentyloxy-4-methoxyphenyl)-2-(1,3,4-oxadiazol-2-yl)ethyl]-5-methylisoindoline-1,3-dione | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 2-[1-(3-Cyclopentyloxy-4-methoxyphenyl)-2-(1,3,4-oxadiazol-2-yl)ethyl]-5-methylisoindoline-1,3-dione, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 17

Tablets, each containing 10 mg 2-[1-(3-cyclopentyloxy-4-methoxyphenyl)-2-(1,3,4-oxadiazol-2-yl)ethyl]-5-methylisoindoline-1,3-dione, can be prepared in the following manner:

| Composition (for 1000 tablets) | |
|---|---|
| 2-[1-(3-cyclopentyloxy-4-methoxyphenyl)-2-(1,3,4-oxadiazol-2-yl)ethyl]-5-methylisoindoline-1,3-dione | 10.0 g |

-continued

| Composition (for 1000 tablets) | |
|---|---|
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 18

Gelatin dry-filled capsules, each containing 100 mg of 2-[1-(3-cyclopentyloxy-4-methoxyphenyl)-2-(1,3,4-oxadiazol-2-yl)ethyl]-5-methylisoindoline-1,3-dione, can be prepared in the following manner:

| Composition (for 1000 capsules) | |
|---|---|
| 2-[1-(3-cyclopentyloxy-4-methoxyphenyl)-2-(1,3,4-oxadiazol-2-yl)ethyl]-5-methylisoindoline-1,3-dione | 100.0 g |
| microcrystalline celluose | 30.0 g |
| sodium lauryl sulfate | 2.0 g |
| magnesium stearate | 8.0 g |

The sodium lauryl sulfate is sieved into the 2-[1-(3-cyclopentyloxy-4-methoxyphenyl)-2-(1,3,4-oxadiazol-2-yl)ethyl]-5-methylisoindoline-1,3-dione through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 19

Gelatin dry-filled capsules, each containing 100 mg of 2-[1-(3-cyclopentyloxy-4-methoxyphenyl)-2-(1,3,4-oxadiazol-2-yl)ethyl]-5-methylisoindoline-1,3-dione, can be prepared in the following manner:

| Composition (for 1000 capsules) | |
|---|---|
| 2-[1-(3-cyclopentyloxy-4-methoxyphenyl)-2-(1,3,4-oxadiazol-2-yl)ethyl]-5- | 5.0 g |

-continued

| Composition (for 1000 capsules) | |
|---|---|
| methylisoindoline-1,3-dione | |
| microcrystalline cellulose | 30.0 g |
| sodium lauryl sulfate | 2.0 g |
| magnesium stearate | 8.0 g |

The sodium lauryl sulfate is sieved into the 2-[1-(3-cyclopentyloxy-4-methoxyphenyl)-2-(1,3,4-oxadiazol-2-yl)ethyl]-5-methylisoindoline-1,3-dione through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

We claim:

1. A compound selected from the group consisting of (a) an oxadiazole of the formula:

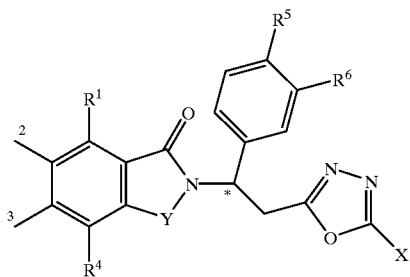

in which:
the carbon atom designated*constitutes a center of chirality;
Y is C=O, $CH_2$, $SO_2$ or $CH_2C$=O;
X is hydrogen, or alkyl of 1 to 4 carbon atoms;
(i) each of $R^1$, $R^2$, $R^3$, and $R^4$, independently of the others, is hydrogen, halo, trifluoromethyl, acetyl, alkyl of 1 to 8 carbon atoms, alkoxy of 1 to 4 carbon atoms, nitro, cyano, hydroxy, —$CH_2NR^8R^9$, —$(CH_2)_2NR^8R^9$, or —$NR^8R^9$; or
(ii) any two of $R^1$, $R^2$, $R^3$, and $R^4$ on adjacent carbon atoms, together with the depicted benzene ring to which they are bound are naphthylidene, quinoline, quinoxaline, benzimidazole, benzodioxole or 2-hydroxybenzimidazole;
each of $R^5$ and $R^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;
(i) each of $R^8$ and $R^9$, independently of the other, is hydrogen, alkyl of 1 to 8 carbon atoms, phenyl, benzyl, pyridyl, pyridylmethyl, or
(ii) one of $R^8$ and $R^9$ is hydrogen and the other is —$COR^{10}$, or —$SO_2R^{10}$, in which $R^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyj, $NR^{11}R^{12}$, or $CH_2NR^{14}R^{15}$, wherein $R^{11}$ and $R^{12}$, independently of each other, are hydrogen, alkyl of 1 to 8 carbon atoms, phenyl, or benzyl and $R^{14}$ and $R^{15}$, independently of each other, are hydrogen, methyl, ethyl, or propyl; or
(iii) $R^8$ and $R^9$ taken together are tetramethylene, pentamethylene, hexamethylene, —CH=NCH=CH—, or —$CH_2CH_2X^1CH_2CH_2$— in which $X^1$ is —O—, —S—, or —NH—; and
(b) the acid addition salts of said oxadiazole containing a nitrogen atom susceptible of protonation.

2. A compound according to claim 1 wherein Y is C=O.
3. A compound according to claim 1 wherein Y is $CH_2$.
4. A compound according to claim 1 wherein each of $R^1$, $R^2$, $R^3$, and $R^4$, independently of the others, is hydrogen, halo, methyl, ethyl, methoxy, ethoxy, nitro, cyano, hydroxy, or —$NR^8R^9$, in which
(i) each of $R^8$ and $R^9$ taken independently of the other is hydrogen or alkyl of 1 to 4 carbon atoms, or
(ii) one of $R^8$ and $R^9$ is hydrogen and the other is —$COCH_3$, —$CONH_2$, —$COCH_2NH_2$, or —$COCH_2N(CH_3)_2$.
5. A compound according to claim 1 wherein one of $R^1$, $R^2$, $R^3$, and $R^4$ is —$NH_2$ and the remaining of $R^1$, $R^2$, $R^3$ and $R^4$ are hydrogen.
6. A compound according to claim 1 wherein one of $R^1$, $R^2$, $R^3$, and $R^4$ is —$NHCOCH_3$, $NHSO_2R^{10}$, or $NHCOR^{10}$ in which $R^{10}$ is as therein defined and the remaining of $R^1$, $R^2$, $R^3$, and $R^4$ are hydrogen.
7. A compound according to claim 1 wherein one of $R^1$, $R^2$, $R^3$, and $R^4$ is methyl or ethyl and the remaining of $R^1$, $R^2$, $R^3$, and $R^4$ are hydrogen.
8. A compound according to claim 1 wherein one of $R^1$, $R^2$, $R^3$, and $R^4$ is —$N(CH_3)_2$ or hydroxy and the remaining of $R^1$, $R^2$, $R^3$, and $R^4$ are hydrogen.
9. A compound according to claim 1 wherein Y is C=O, X is hydrogen, and $R^3$ and $R^4$, taken together, are benzo.
10. A compound according to claim 1 wherein Y is C=O, X is hydrogen, and $R^3$ and $R^4$, taken together, are methylenedioxy.
11. A compound according to claim 1 wherein each of $R^5$ and $R^6$, independently of the other, is methoxy, ethoxy, propoxy, isopropoxy, cyclopentyloxy, cyclohexyloxy, or bicycloalkyloxy.
12. A compound according to claim 1 wherein $R^5$ is alkoxy and $R^6$ is alkoxy, cycloalkyloxy, or bicycloalkyloxy.
13. A compound according to claim 1 wherein $R^5$ is methoxy and $R^6$ is methoxy, ethoxy, or cyclopentyloxy.
14. A compound according to claim 1 wherein $R^5$ is methoxy and $R^6$ is bicycloalkyloxy or benzoalkoxy.
15. A compound according to claim 1 which is 2-isoindoline-1,3-dione, 2-benzoisoindoline-1,3-dione, 2-4-methylisoindoline-1,3-dione, 2-5-methylisoindoline-1,3-dione, 2-5-methylisoindoline-1,3-dione, 2-4-methylisoindoline-1,3-dione, N-1,3-dioxoisoindolin-4-yl]acetamide, N-1,3-dioxoisoindolin-4-yl]acetamide, 5-(tert-butyl)-2-isoindoline-1,3-dione, 2-isoindoline-1,3-dione, 2-isoindolin-1-one, 2-isoindolin-1-one, or 2-3-pyrrolinoquinoline-1,3-dione, said compound being in the form of a substantially chirally pure (R)-isomer, a substantially chirally pure (S)-isomer, or a mixture of the (R)-isomer and (S)-isomer.
16. A compound according to claim 1 wherein two of $R^1$, $R^2$, $R^3$, and $R^4$ are hydrogen and the other two of $R^1$, $R^2$, $R^3$, and $R^4$ are independently halo, trifluoromethyl, acetyl, alkyl of 1 to 8 carbon atoms, alkoxy of 1 to 4 carbon atoms, nitro, cyano, hydroxy, —$CH_2NR^8R^9$, —$(CH_2)_2NR^8R^9$, or —$NR^8R^9$.

17. A compound according to claim 15 wherein two of $R^1$, $R^2$, $R^3$, and $R^4$ are hydrogen and the other two of $R^1$, $R^2$, $R^3$, and $R^4$, are independent alkyl of 1 to 8 carbon atoms, or alkoxy of 1 to 8 carbon atoms.

18. The compound according to claim 1 in the form of the substantially chirally pure (R)-isomer, the substantially chirally pure (S)-isomer, or a mixture of the (R)-isomer and (S)-isomer.

19. A compound according to claim 1 wherein Y is C=O or $CH_2$; each of $R^1$, $R^2$, $R^3$, and $R^4$ independently of the other, is hydrogen, halo, trifluoromethyl, acetyl, alkyl of 1 to 8 carbon atoms, alkoxy of 1 to 4 carbon atoms, nitro, cyano, hydroxy, or $-NR^8R^9$; and any two of $R^1$, $R^2$, $R^3$, and $R^4$ on adjacent carbon atoms, together with the depicted benzene ring to which they are bound are quinoline, quioxaline, 2-$R^{13}$-benzimidazole, benzodioxole or 2-hydroxybenzimidazole, wherein $R^{13}$ is alkyl of 1 to 10 carbon atoms, $-NH_2$, or hydrogen.

20. A pharmaceutical composition comprising a quantity of a compound according to claim 1 in the form of the substantially chirally pure (R)-isomer, the substantially chirally pure (S)-isomer, or a mixture of the (R)-isomer and (S)-isomer, in combination with a carrier, which quantity is at least sufficient upon administration in a single or multiple dose regimen to a mammal having a neoplastic disease, undesirable angiogenesis, or an a disease state in which levels of TNFα, or phosphodiesterase type 4 are elevated, to treat said mammal.

21. A pharmaceutical composition comprising a quantity of a 1 compound according to claim 1 n the form of the substantially chirally pure (R)-isomer, the substantially chirally pure (S)-isomer, or a mixture of the (R)-isomer and (S)-isomer, in combination with a carrier, which quantity is sufficient upon administration in a single or multiple dose regimen to reduce or inhibit undesirable levels of TNFα or matrix metalloproteinases in a mammal.

22. A method of treating a disease state in a mammal in which levels of TNFα are elevated which comprises administering to said mammal an effective amount of a compound according to claim 1 in the form of the substantially chirally pure (R)-isomer, the substantially chirally pure (S)-isomer, or a mixture of the (R)-isomer and (S)-isomer.

23. A method of treating a disease state in a mammal in which levels of phosphodiesterase type 4 are elevated which comprises administering to said mammal an effective amount of a compound according to claim 1 in the form of the substantially chirally pure (R)-isomer, the substantially chirally pure (S)-isomer, or a mixture of the (R)-isomer and (S)-isomer.

24. A method of treating arthritis, rheumatoid arthritis, inflammatory bowel disease, Crohn's disease, aphthous ulcers, cachexia, multiple sclerosis, graft versus host disease, asthma, adult respiratory distress syndrome, or acquired immune deficiency syndrome in a mammal which comprises administering thereto an effective amount of a compound according to claim 1 in the form of the substantially chirally pure (R)-isomer, the substantially chirally pure (S)-isomer, or a mixture of the (R)-isomer and (S)-isomer.

25. A method of treating a mammal having a neoplastic disease which comprises administering to said mammal an effective amount of at least one compound according to claim 1 in the form of the substantially chirally pure (R)-isomer, the substantially chirally pure (S)-isomer, or a mixture of the (R)-isomer and (S)-isomer.

26. A method of treating undesirable angiogenesis in a mammal which comprises administering to said mammal an effective amount of a compound according to claim 1 in the form of the substantially chirally pure (R)-isomer, the substantially chirally pure (S)-isomer, or a mixture of the (R)-isomer and (S)-isomer.

\* \* \* \* \*